(12) United States Patent
Adachi

(10) Patent No.: US 11,358,879 B2
(45) Date of Patent: Jun. 14, 2022

(54) EXCREMENT TREATMENT AGENT

(71) Applicant: Excelsior Inc., Tokyo (JP)

(72) Inventor: Kanichi Adachi, Tokyo (JP)

(73) Assignee: EXCELSIOR INC., Tokyo (JP)

( * ) Notice: Subject to any disclaimer, the term of this patent is extended or adjusted under 35 U.S.C. 154(b) by 399 days.

(21) Appl. No.: 16/603,478

(22) PCT Filed: Mar. 28, 2018

(86) PCT No.: PCT/JP2018/012915
§ 371 (c)(1),
(2) Date: Oct. 7, 2019

(87) PCT Pub. No.: WO2018/190133
PCT Pub. Date: Oct. 18, 2018

(65) Prior Publication Data
US 2021/0122649 A1    Apr. 29, 2021

(30) Foreign Application Priority Data

Apr. 14, 2017 (JP) .............................. JP2017-080854

(51) Int. Cl.
| | |
|---|---|
| *C02F 1/28* | (2006.01) |
| *B01J 20/06* | (2006.01) |
| *B01J 20/12* | (2006.01) |
| *B01J 20/24* | (2006.01) |
| *C02F 103/00* | (2006.01) |

(52) U.S. Cl.
CPC .............. *C02F 1/288* (2013.01); *B01J 20/06* (2013.01); *B01J 20/12* (2013.01); *B01J 20/24* (2013.01); *C02F 2103/005* (2013.01); *C02F 2303/02* (2013.01)

(58) Field of Classification Search
CPC .. C02F 1/288; B01J 20/06; B01J 20/12; B01J 20/24; B01J 20/041; B01J 20/26; A01K 1/0154; A01K 1/0155; A61L 2/18; A61L 9/012
See application file for complete search history.

(56) References Cited

U.S. PATENT DOCUMENTS

| | | | | |
|---|---|---|---|---|
| 6,206,947 | B1 * | 3/2001 | Evans ................... | A01K 1/0152 119/171 |
| 2011/0233105 | A1 * | 9/2011 | Bailey ..................... | C08L 95/00 206/525 |
| 2018/0023167 | A1 * | 1/2018 | Luo ......................... | C22B 1/244 419/35 |
| 2019/0119562 | A1 * | 4/2019 | Mahmoud ................ | C09K 8/05 |
| 2019/0233864 | A1 * | 8/2019 | Carder .................... | C12P 19/02 |
| 2019/0328571 | A1 | 10/2019 | Adachi | |
| 2020/0238302 | A1 * | 7/2020 | Wilson ................ | C08B 37/0057 |

FOREIGN PATENT DOCUMENTS

| | | | |
|---|---|---|---|
| JP | S49-123869 | A | 11/1974 |
| JP | S63-79659 | A | 4/1988 |
| JP | 2003009696 | A * | 1/2003 |
| JP | 2003009696 | A | 1/2003 |
| JP | 2004337533 | A | 12/2004 |
| JP | 2010148444 | A | 7/2010 |
| JP | 2013-006137 | A | 1/2013 |
| JP | 2014087779 | A | 5/2014 |
| JP | 2015168620 | A | 9/2015 |
| JP | 2016179127 | A * | 10/2016 |
| JP | 2016179127 | A | 10/2016 |
| JP | 6226409 | B1 | 11/2017 |

OTHER PUBLICATIONS

International Search Report dated Jun. 19, 2018 for PCT/JP2018/012915 and English translation.
CNIPA, Office Action for the corresponding Chinese patent application No. 201880024829.1, dated Aug. 17, 2021, with English translation.
CIPO, Office Action for the corresponding Canadian patent application No. 3,059,324, dated May 4, 2021.
IPOPHL, Office Action for the corresponding Filipino patent application No. 1/2019/502309.
IP India, Office Action for the corresponding Indian patent application No. 201947040910, dated Aug. 4, 2021.
IP India, Office Action for the corresponding Indian patent application No. 201947040910, dated Mar. 31, 2021, with English translation.
CNIPA, Office Action for the corresponding Chinese patent application No. 201880024829.1, dated Nov. 30, 2021, with English translation.
KIPO, Office Action for the corresponding Korean patent application No. 10-2019-7029514, dated Jun. 24, 2021, with English translation.
KIPO, Office Action for the corresponding Korean patent application No. 10-2019-7029514, dated Dec. 24, 2021, with English translation.

* cited by examiner

*Primary Examiner* — Chester T Barry
(74) *Attorney, Agent, or Firm* — Lucas & Mercanti, LLP

(57) ABSTRACT

An object is to provide an excrement treatment agent, which can suppress not only the odor of feces but also the ammonia odor in various environments. An excrement treatment agent, comprising limonite, lignin and bentonite, wherein, when further comprising slaked lime, the amount of the slaked lime is 10 mass % or less.

11 Claims, No Drawings

US 11,358,879 B2

EXCREMENT TREATMENT AGENT

CROSS REFERENCE TO RELATED APPLICATION

This Application is a 371 of PCT/JP2018/012915 filed on Mar. 28, 2018 which, in turn, claimed the priority of Japanese Patent Application No. 2017-080854 filed on Apr. 14, 2017, both applications are incorporated herein by reference.

TECHNICAL FIELD

The present invention relates to an excrement treatment agent.

BACKGROUND ART

In a prolonged power failure and water cutoff and the like due to disasters such as earthquakes, a toilet cannot be used, and feces and urine are accumulated in each home. A bad odor continues to be emitted from the accumulated feces and urine. When the feces and urine are left, a living environment significantly deteriorates due to an offensive odor thereof. Therefore, a method in which feces and urine are put in a plastic bag and tentatively kept in a sealed state and the like are generally adopted; however, there are problems in that an odor is leaked during storage and a bad odor is emitted around, and the like.

In order to solve these problems, the present inventor proposes a block treatment agent, comprising slaked lime, a water absorbing polymer, a binder, and at least one selected from the group consisting of pH 8-13 phosphates, carbonates and hydroxides (Patent Literature 1).

CITATION LIST

Patent Literatures

Patent Literature 1: JP 2014-87779 A

SUMMARY OF INVENTION

Technical Problem

Because slaked lime with sterilizing properties is essential for a treatment agent in Patent Literature 1, the decomposition of treated excrement hardly occurs. The occurrence of slaked lime dust is also suppressed by using a binder, and health damage is significantly suppressed. From the viewpoint of this, the treatment agent in Patent Literature 1 is particularly good as uses in disaster situations.

It has been found however that, although the treatment agent described in Patent Literature 1 can suppress a bad odor derived from feces due to the action of slaked lime with sterilizing properties, the ammonia odor cannot be suppressed depending on environments.

Therefore, an object of the present invention is to provide an excrement treatment agent, which can suppress not only the odor of feces but also the ammonia odor even under various environments.

Solution to Problem

The present inventor diligently investigated to solve the above problems. As a result, it is found that the above problems can be solved by an excrement treatment agent, comprising limonite, lignin and bentonite, wherein, when the excrement treatment agent further comprises slaked lime, the amount of the slaked lime is 10 mass % or less, thereby completing the present invention.

Advantageous Effects of the Invention

According to the present invention, it is possible to provide an excrement treatment agent which can suppress not only the odor of feces but also the ammonia odor even under various environments.

DESCRIPTION OF EMBODIMENTS

The present invention will now be described. It should be noted that the present invention is not limited only to the following embodiments. In addition, "X to Y" indicating a range means "X or more and Y or less" in the description. In addition, unless otherwise specified, operations and measurement of physical properties and the like were measured at room temperature (20 to 25° C.)/a relative humidity of 40 to 50% RH.

<Excrement Treatment Agent>

The present invention is an excrement treatment agent, comprising limonite, lignin and bentonite, wherein, when the excrement treatment agent further comprises slaked lime, the amount of the slaked lime is 10 mass % or less. According to such constitution, not only the odor of feces but also the ammonia odor can be suppressed even under various environments.

As described above, it has been found that the treatment agent described in Patent Literature 1 can suppress a bad odor derived from feces due to the action of slaked lime with sterilizing properties; however, the occurrence of ammonia can be promoted due to the influence of slaked lime included as an essential component. When the treatment agent is used as uses in disaster situations, feces and urine are put in a plastic bag, that is to say they can be stored in a closed state. Therefore, particularly the ammonia odor cannot be easily a problem. It has been found, however, that even if an offensive odor derived from the odor of feces can be suppressed in the case of an open toilet such as a non-flush toilet, for example a temporary toilet, it is difficult to suppress the ammonia odor.

Therefore, it is found that, when slaked lime can be included, whose amount is 10 mass % or less in an excrement treatment agent, and is combined with limonite, lignin and bentonite, not only the odor of feces but also the ammonia odor can be suppressed, thereby completing the present invention.

The components forming the excrement treatment agent will now be described.

(Limonite)

The excrement treatment agent of the present invention includes limonite.

The chemical composition of limonite is FeO(OH).n$H_2$O, but hematite ($Fe_2O_3$), clay minerals, manganese oxide (II) and the like can be included as impurities. When limonite is included, sulfur compounds such as mercaptan, methyl mercaptan and hydrogen sulfide, and fatty acid compounds, which are bad odor components in feces, can be decomposed and adsorbed.

According to an embodiment of the present invention, limonite is included in the excrement treatment agent in an amount of preferably 1 to 80 mass %, more preferably 5 to 60 mass %, further preferably 10 to 30 mass %, still further preferably 11 to 20 mass %, and still further preferably 12 to 15 mass %. In such range, sulfur compounds and fatty acid compounds can be efficiently decomposed, adsorbed or removed.

According to an embodiment of the present invention, the volume average particle diameter (D50) in the measurement of particle diameter distribution of limonite is preferably 0.1 to 200 μm, more preferably 1 to 150 μm, further preferably 5 to 100 μm, still further preferably 10 to 50 μm, and still further preferably 11 to 30 μm. In such range, the expected effect of the present invention can be efficiently shown.

Limonite can be freely selected from commercially available products. Examples thereof include LMB50, LMB300 (the above are manufactured by JAPAN LIMONITE Co., Ltd.) and the like.

(Lignin)

The excrement treatment agent of the present invention includes lignin. Lignin is a high molecular phenol compound relating to lignification in higher plants, and is also called Mokushitsuso. In the excrement treatment agent of the present invention, lignin is presumed to show the effect of adsorbing and decomposing ammonia and other offensive odor substances. According to an embodiment of the present invention, lignin may be in the form of calcium lignosulfonate, magnesium lignosulfonate, modified calcium lignosulfonate, modified magnesium lignosulfonate, or partially desulfonated sodium lignosulfonate, or the like.

According to an embodiment of the present invention, lignin is included in the excrement treatment agent in an amount of preferably 0.1 to 80 mass %, more preferably 1 to 50 mass %, further preferably 5 to 35 mass %, still further preferably 15 to 32 mass %, still further preferably 20 to 30 mass %, and still further preferably 23 to 29 mass %. In such range, there is the effect of efficiently adsorbing ammonia and other offensive odor substances.

According to an embodiment of the present invention, the average particle diameter of lignin is preferably 1 to 500 μm, more preferably 5 to 300 μm, further preferably 10 to 100 μm, and still further preferably 40 to 80 μm. In such range, ammonia and other offensive odor substances are efficiently adsorbed. Unless otherwise specified, the "average particle diameter" described in the description means an average value obtained by optionally selecting the statistically reliable number of particles, measuring the longest particle diameter of each particle with a microscope, and arithmetically averaging the obtained values. In order to obtain a desired average particle diameter, lignin may be appropriately put through a sieve or the like.

Lignin can be freely selected from commercially available products. Examples thereof include SAN X (such as SAN X P202, SAN X P321, SAN X P252SAN X SCP, and PANILLEX HX), VANILLEX (the above are manufactured by Nippon Paper Industries Co., Ltd.) and the like.

(Bentonite)

The excrement treatment agent of the present invention includes bentonite. Bentonite includes much layered aluminum phyllosilicate, and has properties such as high viscosity, adhesion, water absorption and adsorption. In the excrement treatment agent of the present invention, bentonite adsorbs positive ions such as ammonia, suppresses the occurrence of ammonia and other offensive odor substances and adsorbs them. It is also presumed that, by combining lignin and bentonite, the effect of adsorbing positive ions of bentonite, and a complicated three-dimensional network of lignin, which is still not clear, work in cooperation to further show the effect of suppressing the occurrence of ammonia and other offensive odor substances, and adsorbing and decomposing them.

According to an embodiment of the present invention, bentonite is included in the excrement treatment agent in an amount of preferably 0.1 to 60 mass %, more preferably 1 to 50 mass %, further preferably 5 to 30 mass %, still further preferably 6 to 15 mass %, and still further preferably 7 to 12 mass %. In such range, there is the effect of efficiently adsorbing ammonia and other offensive odor substances.

According to an embodiment of the present invention, the average particle diameter of bentonite is preferably 0.05 to 300 μm, more preferably 0.5 to 200 μm, further preferably 10 to 150 μm and still further preferably 80 to 145 μm.

According to another embodiment of the present invention, the volume average particle diameter (D50) in the measurement of particle diameter distribution of bentonite is preferably 50 to 300 μm, more preferably 80 to 200 μm, and further preferably 100 to 130 μm. In addition, according to another embodiment of the present invention, the modal diameter of bentonite is preferably 50 to 300 μm, more preferably 80 to 200 μm, and further preferably 100 to 180 μm. In such ranges, there is the technical effect of efficiently adsorbing ammonia and other offensive odor substances.

According to an embodiment of the present invention, the percentage of montmorillonite, which is the main component of bentonite, is preferably 70 mass % or more, more preferably 80 mass % or more, still further preferably 90% mass % or more, and still further preferably 95 mass % or more. The components other than the main component are not particularly restricted, and are, for example, clay minerals including quartz, cristobalite, zeolite, feldspar and the like. According to an embodiment of the present invention, the chemical formula or structural formula of bentonite has $Si_8(Al_{3.34}Mg_{0.66})Na_{0.66}O_{20}(OH)_4$. According to an embodiment of the present invention, bentonite contains about 50±15 mass % of silica (particularly crystalline silica). In addition, according to an embodiment of the present invention, the thickness of a single crystal of montmorillonite in bentonite is preferably 0.5 to 5 nm, and more preferably 0.8 to 3 nm. According to an embodiment of the present invention, the width of a single crystal of montmorillonite in bentonite is preferably 50 to 2000 nm, more preferably 80 to 1500 nm, and further preferably 100 to 1000 nm. According to an embodiment of the present invention, the shape of montmorillonite in bentonite is a flat plate shape.

Bentonite as described above can be freely selected from commercially available products. Examples of commercially available bentonite can include KUNIPIA-F, KUNIMINE-F, MOISTNITE-S, MOISTNITE-U (the above are manufactured by KUNIMINE INDUSTRIES CO., LTD.), 250SA-B (the above is manufactured by Hoyo Bentonite Kogyo K.K.) and the like.

(Slaked Lime)

The excrement treatment agent of the present invention is characterized by including slaked lime, and the amount thereof is 10 mass % or less in the excrement treatment agent. The preferred upper limit of the amount of slaked lime is 9 mass % or less, more preferably 8 mass % or less, further preferably 7 mass % or less, still further preferably 6 mass % or less, and still further preferably 5 mass % or less. When the upper limit is 10 mass % or less, ammonia can be suppressed. On the other hand, the lower limit is 0 mass %, and may be 1 mass % or more, 2 mass % or more, and 3 mass % or more. When slaked lime is included, there is the effect of suppressing the odor of feces and destroying microorganisms. By offsetting a weakness of slaked lime when adding slaked lime to the excrement treatment agent (which is to promote the occurrence of ammonia) by limonite, lignin and bentonite (particularly limonite), the odor of feces and ammonia odor can be suppressed.

According to an embodiment of the present invention, the average particle diameter of slaked lime is 10 µm or more, and more preferably 50 µm or more. The upper limit is also not particularly restricted, and is, for example, 1000 µm or less, preferably 500 µm or less, more preferably 300 µm or less, and further preferably 150 µm or less. In addition, according to an embodiment of the present invention, the average particle diameter is preferably 10 to 300 µm, preferably 20 to 150 µm, and preferably 50 to 100 µm. In such range, there is the technical effect of removing sulfur compounds, which are bad odor substances in feces.

As a method for preparing slaked lime, it is preferred to purchase a commercially available product, and examples thereof are preferably those from Ube Material Industries, Ltd. and the like.

(Water Absorbing Polymer)

The excrement treatment agent of the present invention can include a water absorbing polymer.

The water absorbing polymer (water absorbing agent) which can be included in the excrement treatment agent of the present invention has a role to help limonite, lignin, bentonite, and not more than a certain amount of slaked lime, and also to make the pH of an object to be treated towards neutral. In the present invention, moisture in feces and urine can be absorbed and solidified by including a water absorbing polymer. In addition, an object to be treated is solidified by the action of the water absorbing polymer, and the solidified object is covered with the components forming the excrement treatment agent, and the expected effect of the present invention can be more efficiently shown.

Specific examples of the water absorbing polymer used in the present invention include, for example, starch-based water absorbing polymers such as starch acrylonitrile graft polymer hydrolysate and starch acrylic acid graft copolymer, cellulose-based water absorbing polymers such as cellulose-acrylonitrile graft polymer and cellulose-styrenesulfonic acid graft copolymer, polysaccharide-based water absorbing polymers, protein-based water absorbing polymers such as collagen, polyvinyl alcohol-based water absorbing polymers such as polyvinyl alcohol cross-linked polymer, acrylic water absorbing polymers such as cross-linked sodium polyacrylate, cross-linked acrylic acid and sodium acrylate copolymer, and sodium acrylate-vinyl alcohol copolymer, maleic anhydride-based water absorbing polymers, vinyl pyrrolidone-based water absorbing polymers, and polyether-based water absorbing polymers such as polyethylene glycol.diacrylate cross-linked polymer, and the like. These water absorbing polymers may be used alone or two or more polymers may be used in combination. In addition, these water absorbing polymers may be synthesized or a commercially available product may be used. Examples of commercially available products include, for example, AQUA KEEP (registered trademark) SA (manufactured by Sumitomo Seika Chemicals Company, Limited.), AQUALIC (registered trademark) CA (manufactured by NIPPON SHOKUBAI CO., LTD.), SANFRESH (ST-250, ST-100, ST-573), AQUAPEARL (manufactured by San-Dia Polymers, Ltd.), Himosab HS-960 (manufactured by HYMO CORPORATION) and the like.

In addition, in an embodiment of the present invention, the water absorbing polymer may be a carboxymethylcellulose. Carboxymethylcellulose is a cellulose derivative with carboxymethyl groups ($-CH_2-COOH$) bound to some of the hydroxy groups of the gluconopyranose monomers which form the cellulose backbone. In addition, this carboxymethylcellulose may be a carboxymethylcellulose salt. Carboxymethylcellulose has high affinity for water and is a thickener which becomes a gel-like high viscosity body by being mixed with water. In the present invention, because the viscosity of the treatment agent increases, the effect of suppressing a bad odor is high and moreover the suppressing effect can be maintained.

The average particle diameter of the water absorbing polymer which can be included in the excrement treatment agent of the present invention is also not particularly restricted, and is preferably 50 to 1000 µm, more preferably 80 to 850 µm, further preferably 100 to 600 µm, still further preferably 200 to 500 µm, still further preferably 250 to 450 µm, and still further preferably 300 to 400 µm. In addition, in a preferred embodiment of the present invention, the amount of water absorbing polymer with 106 µm or less is preferably 20 mass % or less, more preferably 15 mass % or less, and still further preferably 12 mass % or less. In addition, the amount of water absorbing polymer with above 106 µm and 850 µm or less is preferably 80 mass % or more, and more preferably 85 mass % or more. In addition, the amount of water absorbing polymer with above 850 µm is preferably 10 mass % or less, more preferably 5 mass % or less, and further preferably 3 mass % or less.

According to an embodiment of the present invention, the water absorbing polymer is included in the excrement treatment agent in an amount of preferably 1 to 90 mass %, more preferably 20 to 70 mass %, and further preferably 30 to 60 mass %. In such range, there is the effect of solidifying moisture in feces and urine and preventing diffusion.

The excrement treatment agent in an embodiment of the present invention may be granulated using a binder such as water, PVA, water-soluble cellulose, water-soluble carboxymethylcellulose or sodium alginate, and the like. In addition, the excrement treatment agent in an embodiment of the present invention may be a granular treatment agent or a block treatment agent using a technique in Japanese Unexamined Patent Application Publication No. 2013-6137 or Re-publication of PCT International Publication No. 2011/162244.

<Method for Producing Excrement Treatment Agent>

In the present invention, there is provided a method for producing an excrement treatment agent, the method having mixing limonite, lignin, bentonite and slaked lime, and having mixing them so that the amount of the slaked lime is 10 mass % or less.

The method for producing an excrement treatment agent has mixing the components which form the excrement treatment agent. The order of mixing the above components is not particularly restricted, and the components may be mixed at once or the components may be mixed sequentially.

<Uses of Excrement Treatment Agent, Method for Using it, Etc.>

According to an embodiment of the present invention, the excrement treatment agent is suitable for an open toilet such as a non-flush toilet, for example a temporary toilet. Therefore, according to an embodiment of the present invention, the excrement treatment agent is used for a non-flush toilet. That is to say, the excrement treatment agent of the present invention can suppress not only the odor of feces but also the ammonia odor (and moreover can suppress them over a long period of time), and thus can be suitably used for a non-flush toilet (temporary toilet). (Even when zeolite is used in place of bentonite, the ammonia odor cannot be suppressed over a long period of time).

In an embodiment of the present invention, when applied to a non-flush toilet such as a temporary toilet, the excrement treatment agent of the present invention is preferably put in a receptacle for feces and urine in advance. By such embodiment, a toilet user does not require to directly add the excrement treatment agent.

In addition, in an embodiment of the present invention, when the excrement treatment agent of the present invention is put in a receptacle for feces and urine in advance, it is preferred that a small amount of water be also added. By such embodiment, the excrement treatment agent can be also granulated. By doing this, the dust of the excrement treatment agent can be suppressed, and a user can use a toilet in a comfortable way.

In addition, in an embodiment of the present invention, for non-flush toilets in an area with undeveloped sewerage infrastructure (for example, a toilet using a hole dug in e.g. soil as a receptacle for feces and urine), it is preferred that the excrement treatment agent of the present invention be put in the hole in advance. Here, the excrement treatment agent of the present invention is formed by including limonite, lignin and bentonite. Because these components do not have a bad effect on soil, when the hole is filled with feces and urine, feces and urine can be treated only by covering over the hole with soil. Furthermore, the positive effect of feces and urine components and components derived from the excrement treatment agent on soil can lead to soil improvement. In an embodiment of the present invention, the same effect can be expected by using a biodegradable water absorbing polymer, for example starch-based, as a water absorbing polymer.

In addition, in an embodiment of the present invention, when the excrement treatment agent includes a water absorbing polymer, it is preferred that, for example, a component to destroy the structure of a water absorbing polymer such as hypochlorous acid or calcium chloride be added to treated feces and urine. By such embodiment, solidified feces and urine are changed into a liquid form, which can be also used for a fertilizer and the like by spraying or scattering on soil.

Because the excrement treatment agent of the present invention shows the effect even in such severe environment, of course, it can be also used as a treatment agent for pet feces and urine. Therefore, in an embodiment of the present invention, the excrement treatment agent is used to treat pet excrement. In the present embodiment, the components forming the excrement treatment agent are included in a water-soluble base material. By such embodiment, a pet owner does not require to carry an excrement treatment agent in the form of powder, and portability is improved. In addition, in the present embodiment, the excrement treatment agent included in a water-soluble base material can be directly added to a bag (for example, plastic bag) in which pet excrement is stored. In this case, it is more preferred that a small amount of water be further added. According to such embodiment, it is very easy to treat pet feces and urine, and the odor problem can be also solved. In addition, in an embodiment of the present invention, a water-soluble base material including the excrement treatment agent is opened by cutting apart thereof, and the excrement treatment agent in the form of powder which has been stored in the water-soluble base material may be scattered on pet excrement. By such embodiment, the expected effect of the present invention can be efficiently shown even when water is not added.

Here, the water-soluble base material is not particularly restricted as long as the base material is soluble in water, and examples thereof include water-soluble paper, water-soluble film and the like. The size of the water-soluble base material is not particularly restricted.

In addition, the excrement treatment agent of the present invention which efficiently shows the desired effect even in such severe environment (particularly an open toilet) can be used as a treatment agent for uses in disaster situations. In this case, a bag (for example plastic bag) in which treated excrement has been put is supposed to be bound. Moreover, the excrement treatment agent can be used to treat livestock excrement, organic sludge and vomited excrement.

In a preferred embodiment of the present invention, the amount of an excrement treatment agent to an object to be treated (150 to 350 g of feces) can be appropriately adjusted as needed, and is as a guide preferably 3 to 100 g, more preferably 5 to 70 g, and further preferably 10 to 50 g. The amount of an excrement treatment agent to an object to be treated (50 to 500 g of urine) can be appropriately adjusted as needed, and is as a guide preferably 3 to 100 g, more preferably 5 to 70 g, and further preferably 10 to 50 g.

EXAMPLES

The present invention will now be further described by way of typical embodiments of the present invention. Needless to say, the present invention is not limited to these embodiments. Unless otherwise specified, "parts" and "%" in examples indicate "parts by mass" and "mass %" respectively. In addition, unless otherwise specified, operations and measurement of physical properties and the like were measured at room temperature (20 to 25° C.)/a relative humidity of 40 to 50% RH.

<Production of Excrement Treatment Agent>

Example 1, Comparative Examples 1 to 10

Components forming an excrement treatment agent were mixed so that a composition shown in Table 1 was obtained to produce 35 g of an excrement treatment agent.

Comparative Example 11

An excrement treatment agent, 35 g, was produced in the same manner as in Example 1 except that the composition was changed to the same composition as in Example 19 in Japanese Unexamined Patent Application Publication No. 2014-87779.

<Offensive Odor Test and Measurement of Ammonia>

To a polyethylene bag, 200 g of feces and 100 g of urine from a male in his forties were added, and the bag was sealed and left to stand for an hour.

The bag was opened, and 35 g of an excrement treatment agent produced in each Example and each Comparative Example was added thereto. The bag was left to stand for 30 days and a sensory test for an offensive odor was then carried out. In addition, using a detector tube (ammonia gas detector tube (KITAGAWA) (manufactured by KOMYO RIKAGAKU KOGYO K.K.), the measurement limit is up to 200 ppm), the concentration of ammonia was measured (shown in Table 1).

TABLE 1

| | LIMONITE LMB-50 | LIGNIN SAN X P-202 | BENTONITE KUNIPIA-F | BENTONITE MOISTNITE-S | SLAKED LIME UBE MATERIALS | ZEOLITE ZEOFILL W1 | WATER ABSORBING POLYMER POLYACRYLIC ACID-BASED POLYMER | WATER ABSORBING POLYMER STARCH-BASED POLYMER | OFFENSIVE ODOR | AMMONIA (PPM) |
|---|---|---|---|---|---|---|---|---|---|---|
| EXAMPLE 1 TBS-36 | 13.70% | 27.40% | — | 8.22% | 4.11% | — | — | 46.57% | ⊚ | 10 |
| COMPARATIVE EXAMPLE 1 TBS-33 | 15.63% | 31.25% | — | — | — | — | — | 53.12% | △ | 0 |
| COMPARATIVE EXAMPLE 2 TBS-34 | 31.25% | 15.63% | — | — | — | — | — | 53.12% | △ | 0 |
| COMPARATIVE EXAMPLE 3 TBS-31 | 12.05% | 24.10% | 3.61% | 3.61% | 12.05% | 3.61% | — | 40.97% | ○ | 200 OR MORE |
| COMPARATIVE EXAMPLE 4 TBS-1 | 100.00% | — | — | — | — | — | — | — | X | NOT MEASURED |
| COMPARATIVE EXAMPLE 5 TBS-2 | 50.00% | — | — | — | — | — | 50.00% | — | X | 60 |
| COMPARATIVE EXAMPLE 6 TBS-11 | 33.33% | — | — | — | 10.00% | — | 56.67% | — | △ | 170 |
| COMPARATIVE EXAMPLE 7 TBS-14 | 35.09% | — | — | — | 5.26% | — | 59.65% | — | △ | 80 |
| COMPARATIVE EXAMPLE 8 TBS-15 | 28.99% | 8.70% | 4.55% | — | 4.35% | 8.70% | 49.26% | — | ○ | 70 |
| COMPARATIVE EXAMPLE 9 TBS-26 | 30.3% | — | 4.55% | 4.55% | 4.55% | 4.55% | — | 51.50% | ○ | 46 |
| COMPARATIVE EXAMPLE 10 TBS-37 | — | 31.75% | 4.76% | 4.76% | 4.55% | 4.76% | — | 53.97% | X | 30 |
| COMPARATIVE EXAMPLE 11 | | | | | | | | | ○ | 200 OR MORE |

Limonite: LMB-50, volume average particle diameter (D50): 22 μm,
Lignin: SAN X P-202, average particle diameter: 60 μm
KUNIPIA-F, average particle diameter: 139 μm,
MOISTNITE-S, average particle diameter: 139 μm,
Slaked lime: manufactured by Ube Material Industries, Ltd.: 100-mesh sieved slaked lime, Zeolite, ZEOFILL W1, volume average particle diameter (D50): 13 μm,
Polyacrylic acid-based polymer, SANFRESH ST-250, average particle diameter: 380 μm (above 850 μm, about 1 mass %; above 106 μm and 850 μm or less, 89 mass %; 106 μm or less, about 10 mass %),
Starch-based polymer, SANFLESH ST-100, average particle diameter: 380 μm (above 850 μm, about 1 mass %; above 106 μm and 850 μm or less, 89 mass %; 106 μm or less, about 10 mass %).
⊚: almost odorless
○: an offensive odor remains
△: an offensive odor is rather strong
X: an offensive odor is strong (bad odor)

<Results and Consideration>

When using the excrement treatment agent in Example 1, even in a case where treated excrement was left to stand over a long period of time, 30 days, not only the odor of feces but also the ammonia odor could be suppressed, and an offensive odor was hardly perceived. On the other hand, Comparative Examples 1 and 2 did not include slaked lime, and thus ammonia did not originally occur very much. Lignin was also included, and thus ammonia could not be observed. However, a rather strong odor of feces remained. Therefore, it is suggested that the existence of bentonite is important to show the expected effect of the present invention.

In Comparative Example 3, the ratio of slaked lime is above 10 mass % in the excrement treatment agent, and thus the concentration of ammonia was high. Therefore, the odor of feces was suppressed due to the action of limonite, lignin, bentonite, slaked lime and the like; however, an irritating odor derived from ammonia was strong, and an offensive odor remained.

Comparative Example 4 is an experiment which uses only limonite; accordingly, a bad odor like fermented raw garbage was perceived.

Comparative Example 5 is an experiment in which a water absorbing polymer is added to one half of the composition in Comparative Example 4. The offensive odor was lower than that in Comparative Example 4 because moisture was absorbed; however, a bad odor like fermented raw garbage was still perceived.

In Comparative Examples 6 and 7, the composition of Comparative Example 5 was used as a base, and slaked lime was added thereto. Therefore, the occurrence of ammonia was promoted, and a rather strong offensive odor, in which the irritating odor of ammonia and organic odor are combined, was emitted in both cases.

In Comparative Example 8, the composition is close to that in Example but bentonite is not included. Accordingly, an offensive odor, in which the irritating odor of ammonia and organic odor are combined, remained as the offensive odor. In other words, it is suggested that limonite, lignin and bentonite work in cooperation to show the expected effect of the present invention. It is further suggested that the expected effect of the present invention cannot be shown in the combination of limonite, lignin and zeolite, and the combination of limonite, lignin and bentonite is important. In other words, zeolite cannot be an alternative for bentonite in the present invention.

Comparative Example 9 did not include lignin, and thus the occurrence of ammonia cannot be suppressed, and also an offensive odor from the odor of feces remained. Comparative Example 10 did not include limonite, and thus a bad odor was significant.

Comparative Example 11 included a large amount of slaked lime, and thus the odor of feces was hardly perceived. However, the occurrence of ammonia was promoted as alternated, and an offensive odor remained.

This application is based on Japanese patent application No. 2017-80854 filed on Apr. 14, 2017, the disclosed contents of which are incorporated herein by reference in its entirety.

The invention claimed is:

1. An excrement treatment agent, comprising
limonite in an amount of 11 mass % or more,
lignin in an amount of 5 mass % or more,
bentonite in an amount of 1 mass % or more, and
a water-absorbing polymer in an amount of 20 mass % or more,
wherein, when the excrement treatment agent further comprises slaked lime, an amount of the slaked lime is 10 mass % or less.

2. The excrement treatment agent according to claim 1, wherein the amount of the limonite is in a range of 11 to 60 mass %.

3. The excrement treatment agent according to claim 1, wherein the amount of the lignin is in a range of 5 to 50 mass %.

4. The excrement treatment agent according to claim 1, wherein the amount of the bentonite is in a range of 1 to 60 mass %.

5. The excrement treatment agent according to claim 1, wherein the water-absorbing polymer is a starch-based water absorbing polymer.

6. The excrement treatment agent according to claim 1, wherein the amount of the lignin is 15 mass % or more.

7. The excrement treatment agent according to claim 1, wherein the amount of the lignin is 20 mass % or more.

8. The excrement treatment agent according to claim 1, wherein the amount of the slaked lime is in a range of 1 to 10 mass %.

9. The excrement treatment agent according to claim 1,
wherein the amount of the limonite is in a range of 11 to 60 mass %,
the amount of the lignin is in a range of 5 to 50 mass %,
the amount of the bentonite is in a range of 1 to 60 mass %,
the amount of the water-absorbing polymer is in a range of 20 to 70 mass %.

10. A granule comprising the excrement treatment agent according to claim 1 and a binder.

11. A method comprising:
placing the excrement treatment agent according to claim 1 in a receptacle for feces and urine of a non-flush toilet.

* * * * *